(12) United States Patent  
Leinweber et al.

(10) Patent No.: US 9,334,243 B2  
(45) Date of Patent: May 10, 2016

(54) N-ALKYL-N'-POLY(OXYALKYL)HEXA-HYDROPYRIMIDINE-QUATERNARY AMMONIUM SALTS AND THE USE THEREOF AS CORROSION INHIBITORS

(71) Applicants: Dirk Leinweber, Kelkheim (DE); Hannah Benson, Heppenheim (DE); Nihal Obeyesekere, Houston, TX (US); Thenuka Ariyaratna, Kingwood, TX (US)

(72) Inventors: Dirk Leinweber, Kelkheim (DE); Hannah Benson, Heppenheim (DE); Nihal Obeyesekere, Houston, TX (US); Thenuka Ariyaratna, Kingwood, TX (US)

(73) Assignee: Clariant International Ltd., Muttenz (CH)

( * ) Notice: Subject to any disclaimer, the term of this patent is extended or adjusted under 35 U.S.C. 154(b) by 132 days.

(21) Appl. No.: 14/055,644

(22) Filed: Oct. 16, 2013

(65) Prior Publication Data

US 2015/0104349 A1    Apr. 16, 2015

(51) Int. Cl.  
*C23F 11/00* (2006.01)  
*C23F 11/04* (2006.01)  
(Continued)

(52) U.S. Cl.  
CPC ................ *C07D 239/04* (2013.01); *C09K 8/54* (2013.01); *C23F 11/141* (2013.01); *C09K 2208/32* (2013.01)

(58) Field of Classification Search  
CPC .............. A61L 2/00; C23F 11/00; C02F 5/00  
USPC ........ 422/7, 14, 16–17; 134/6, 8, 22.1, 22.13; 252/175, 387  
See application file for complete search history.

(56) References Cited

U.S. PATENT DOCUMENTS 5,530,131 A * 6/1996 Hoffmann et al. ............ 544/335

*Primary Examiner* — Monzer R Chorbaji  
(74) *Attorney, Agent, or Firm* — Todd A. Waldrop

(57) ABSTRACT

This invention relates to N-alkyl-N'-poly(oxyalkyl)hexapyrimidine-quaternary ammonium salts of the formulae (Ia)-(Ic) and mixtures thereof

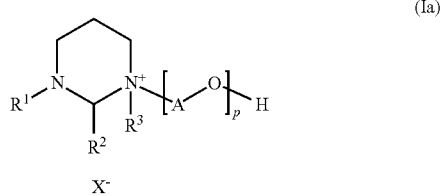

(Ia)

-continued

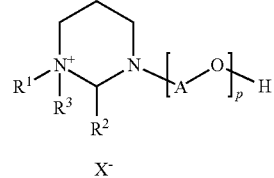

(Ib)

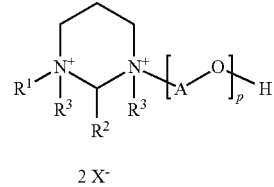

(Ic)

in which  
$R^1$ is $C_8$-$C_{30}$-alkyl or $C_8$-$C_{30}$-alkenyl,  
$R^2$ is hydrogen, $C_1$-$C_3$-alkyl, —COOH or a group selected from the formulae

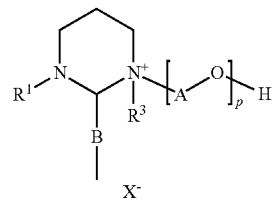

(Id)

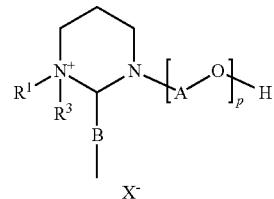

(Ie)

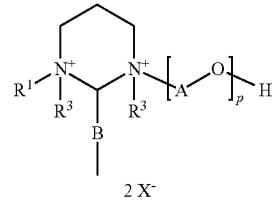

(If)

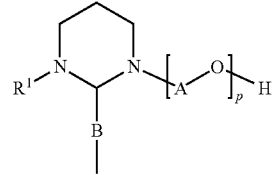

(Ig)

wherein  
the bonding occurs via the valence containing the B residue,  
B is a single bond or a $C_1$ to $C_3$ alkylene group  
$R^3$ is $C_1$-$C_4$-alkyl, vinyl or allyl,  
$X^-$ is methylsulfate or iodide,  
A is a 1,2-alkylene group having from 2 to 10 carbon atoms, and  
p is a number from 1 to 50.

10 Claims, No Drawings

(51) Int. Cl.
*C09K 3/00* (2006.01)
*C02F 5/02* (2006.01)
*B08B 9/00* (2006.01)
*B08B 7/00* (2006.01)
*C07D 239/04* (2006.01)
*C09K 8/54* (2006.01)
*C23F 11/14* (2006.01)

N-ALKYL-N'-POLY(OXYALKYL)HEXA-HYDROPYRIMIDINE-QUATERNARY AMMONIUM SALTS AND THE USE THEREOF AS CORROSION INHIBITORS

Corrosion is a serious and challenging problem in the oil and gas industry and its prevention is acute in offshore operations. Water, acidic gases such as hydrogen sulfide and carbon dioxide, organic acids, and oxygen contribute to the corrosion of mild steel, and other types of alloys used in the oil and gas industry. Corrosion can cause oil and gas to leak from flowlines which can lead to explosions, accidents, and environmental disasters. Corrosion inhibitors are essential for preventing uncontrolled discharge of oil and/or gas into the environments surrounding the flowlines.

Corrosion inhibitors are either water-soluble or oil soluble chemical compounds. When added in small quantities to an aggressive medium, these chemicals inhibit corrosion by changing the surface conditions of the metal. The major factors controlling corrosion rates are $CO_2$, $H_2S$, S, polysulfides, organic acids, composition of liquids, flow conditions, inorganic anions, such as chlorides, oxygen, and temperature. Sweet systems that contain very little or no $H_2S$ can be treated easily by using corrosion inhibitors. Mitigating corrosion in systems that produce high levels of $H_2S$ with $CO_2$ are difficult because these systems can produce elemental sulfur and polysulfides, which tend to cause localized rather than general corrosion. Understanding the different conditions that control the flow in flowlines, the conditions that cause corrosion and the various environmental and safety restrictions for chemical usage in different parts of the world are all important factors when designing corrosion inhibitors. Sour gas corrosion is unique and the corrosion inhibitors suitable for sweet corrosion are not highly effective in mitigating sour gas corrosion.

The production of sour gas in oil fields increases the corrosivity of the produced fluids. The mechanism of corrosion in an aqueous solution containing $CO_2$ is quite different from the mechanism of corrosion in sour gas systems. In sour gas reservoirs, elemental sulfur, polysulfides, water and $CO_2$ exist with hydrogen sulfide. Elemental sulfur can be carried out with hydrogen sulfide by dissolving in $H_2S$ or by chemically binding to hydrogen sulfide gas as $H_2S_x$. Elemental sulfur dissolved in sour gas can be released as elemental sulfur by changes in temperature and pressure. When flowlines are plugged with elemental sulfur, it produces a problem that is equally as serious as is the corrosivity caused by these compounds. Controlling deposition of elemental sulfur is as important as mitigating the corrosion in flowlines.

All these factors drive a continuous need for improved corrosion inhibitors.

US2004/0169161 A1 discloses the use of doubly alkoxylated quaternary compounds as corrosion inhibitors with improved water solubility and improved film persistence.

US2005/0156137 A1 discloses nitrogen-containing hydroxyethyl substituted compounds as corrosion inhibitors to be used under sweet-well conditions as well as under sour-well conditions.

DE2813047 A1 and CA 1084685 are disclosing the use of quaternary pyridinium salts as corrosion inhibitors under sour gas conditions.

The problem to be solved by innovation was to synthesize improved corrosion inhibitors particularly suitable for sour gas environments.

US-005530131A describes N-alkyl-N'-poly(oxyalkyl)-hexahydropyrimidines of the formula

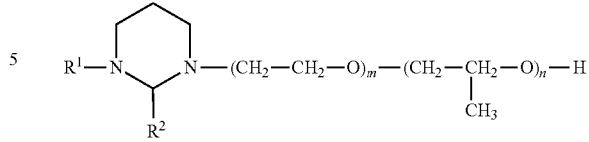

in which:
$R^1$ is $C_1$-$C_{30}$-alkyl or $C_2$-$C_{30}$-alkenyl,
$R^2$ is hydrogen or $C_1$-$C_3$-alkyl,
A is a 1,2-alkylene group having from 2 to 10, preferably from 2 to 5, carbon atoms and
m is a number from 0 to 50
n is a number from 0 to 50,
m+n is between 1 and 50, and
further provides for the use of N-alkyl-N'-poly(oxyalkyl) hexahydropyrimidines of the formula (X) as corrosion inhibitors in water/oil emulsions as are present in petroleum.

It has now been found that use of N-alkyl-N'-poly(oxyalkyl)hexahydropyrimidine-quaternary ammonium salts give excellent corrosion-protection for water/oil emulsions as they are present in petroleum. Particularly in sour-gas (hydrogen sulfide) environments, these compounds show improved corrosion inhibition properties when compared with conventional sour gas corrosion inhibitors such as alkyl pyridine quaternary compounds.

The invention provides N-alkyl-N'-poly(oxyalkyl)hexahydropyrimidine-quaternary ammonium salts of the formulae (Ia)-(Ic)

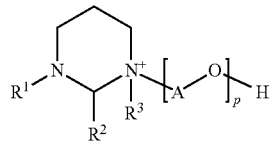

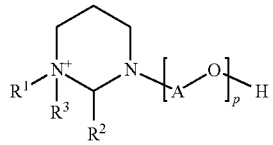

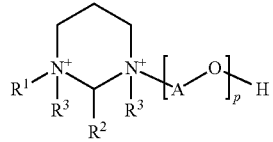

in which
$R^1$ is $C_8$-$C_{30}$-alkyl or $C_8$-$C_{30}$-alkenyl,
$R^2$ is hydrogen, $C_1$-$C_3$-alkyl, —COOH or a group selected from the formulae

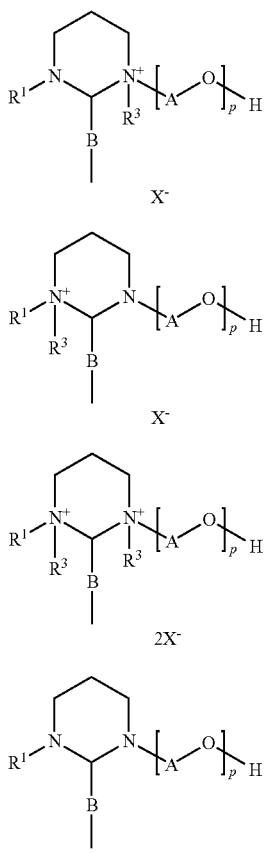

(Id)

(Ie)

(If)

(Ig)

wherein
the bonding occurs via the valence containing the B residue,
B is a single bond or a $C_1$ to $C_3$ alkylene group,
$R^3$ is $C_1$-$C_4$-alkyl, vinyl, allyl or benzyl,
$X^-$ is a counterion,
A is a 1,2-alkylene group having from 2 to 10 carbon atoms and
p is a number from 1 to 50.

In another aspect of the invention, there is provided the use of one or more of compounds of formulae (Ia)-(Ic) as a corrosion inhibitor. Such use is preferably performed during the production and/or processing of crude oil and natural gas, particularly in the presence of sour gas.

In another aspect of the invention there is provided a process for inhibiting corrosion of metal. The process comprises bringing the metal into contact with one or more of the compounds according to the formulae (Ia)-(Ic). The process is preferably applied to metal which is in contact with sour gas during crude oil or natural gas production or processing.

Depending on the origin of the primary amine used in the synthesis of the compound (I), $R^1$ is preferably a radical of a naturally occurring fatty acid. Since the amines which are used in the synthesis of the compounds (Ia) to (Ic) and in which $R^1$ is an alkyl or alkenyl group are generally random mixtures of homologs and also of isomers, $R^1$ will usually be a mixture of different alkyl and/or alkenyl groups having various chain lengths. The number of carbon atoms given for $R^1$ shall therefore be understood as an average number.

Preference is given to compounds (I) in which $R^1$ is an alkyl or alkenyl group having from 8 to 24 carbon atoms, in particular having from 10 to 18 carbon atoms, especially those having from 12 to 18 carbon atoms. Particularly advantageous radicals $R^1$ are those which can be traced back to the $C_{10}$ fraction, the $C_{10}/C_{12}$ fraction, the, the $C_{12}/C_{14}$, or the $C_{16}/C_{18}$ fractions of a primary amine.

Examples of straight-chain or branched alkyl and alkenyl groups $R^1$ which may be mentioned are: n-octyl, 2-ethylhexyl, n- and iso-nonyl, n- and iso-decyl, n-undecyl, n-dodecyl, n-tetradecyl, n-hexadecyl, n-octadecyl, oleyl, linoleyl, linolenyl and behenyl.

In the case where $R^2$ has the meaning of formulae (1d) to (1g), the inventive compounds have a structure like e.g. (for B=single bond)

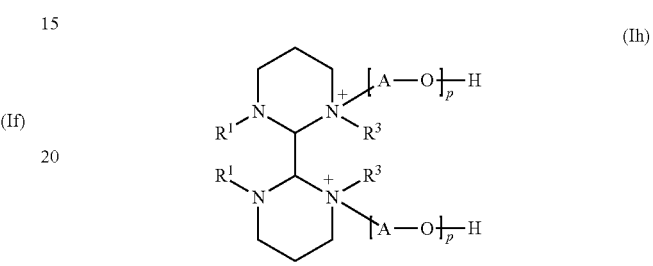

(Ih)

This is an exemplary structure. It is within the scope of this invention to have structures similar to formula (Ih) wherein $R^1$, $R^3$, A and p have different meanings in the two parts of the molecule linked by the B substituent.

A has preferably 2 to 5 carbon atoms, the 1,2-alkylene group A is preferably an ethylene group or a propylene, 1,2-butylene or 2,3-butylene group. Here, each group A can also be a random mixture of a plurality of the specified 1,2-alkylene groups, mixtures of ethylene and propylene units being preferred.

The degree of alkoxylation p is between 1 and 50, preferably from 3 to 35, in particular from 5 to 15. The values of p are usually averages.

$R^3$ is preferably methyl.

The counterion $X^-$ is, in a preferred embodiment and halogenide-ion, an organo sulfate $R-O-SO_3^-$ or an organo carbonate $R-O-CO_2^-$. In particular it is chloride, bromide, iodide, methyl sulfate, ethyl sulfate or methyl carbonate.

In one preferred embodiment, X does not mean chloride when A means ethylene, $R^2$ means hydrogen and $R^3$ means methyl.

In another preferred embodiment, X does not mean chloride when A means ethylene. $R^2$ means hydrogen, $R^3$ means methyl and $R^1$ is a tallow fatty residue. The tallow fatty residue is a mixture of aliphatic hydrocarbons having the following composition, according to Ullmann's Encyclopedia of Industrial Chemistry, 2012: (percentages are wt.-%).

| | |
|---|---|
| C14:0 | 1-4% |
| C16:0 | 22-30% |
| C16:1 | 2-4% |
| C18:0 | 15-35% |
| C18:1 | 26-56% |
| C18:2 | 2-7% |
| C18:3 | 1-2% |
| C20:0 | <0.5% |

The compounds of the formulae (Ia)-(Ic) of the invention are generally obtained by N-alkylation of N-alkyl-N'-poly(oxyalkyl)-hexahydropyrimidines of the formula (II)

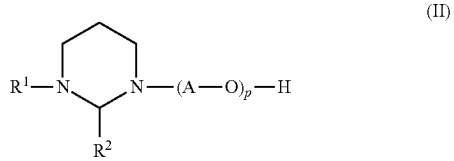

whose preparation is described in US-005530131A. The N-alkylation of the compounds of the formula (II) is carried out by methods known per se.

Suitable methods are known, for example, from Jerry March, "*Advanced organic chemistry*" (John Wiley & Sons, 1985, $3^{rd}$ edition).

Suitable N-alkylating agents are for example Dimethyl sulfate, Diethyl sulfate, Dimethyl carbonate, Methyl iodide, Methyl chloride, allyl bromide or benzyl chloride. Preferably, N-alkyl-N'-poly(oxyalkyl)-hexahydropyrimidine and N-alkylating agent are reacted in equimolar amounts at temperatures in the range from 50-85° C. Advantageously, the N-alkyl-N'-poly(oxyalkyl)-hexahydropyrimidine is initially charged, heated to 50-60° C. and the N-alkylating agent is added. The reaction is exothermic and it should be avoided that the reaction mixture is heated to >85° C. The reaction mixture is stirred, preferably at 80° C., in order to obtain complete conversion to the desired product of the formulae (Ia)-(Ic) or product mixture thereof.

If an equimolar amount or less than an equimolar amount of N-alkylating agent is used, a mixture of starting material (N-alkyl-N'-poly(oxyalkyl)-hexahydropyrimidine) and substances of the formulae (Ia)-(Ic) is obtained. If more than an equimolar amount of N-alkylating agent is used, a mixture of substances of the formulae (Ia)-(Ic) is obtained. The expression equimolar means one mole N-alkylating agent per mole of starting material.

If $R^2$=H or $C_1$-$C_4$-alkyl and two equivalents of alkylating agents are used, a nearly complete conversion to compound (Ic), with $R^2$=H or $C_1$-$C_4$-alkyl is observed.

If $R^2$=a group selected from the formulae (Id)-(Ig) and four equivalents of alkylating agents are used, a nearly complete conversion to compound (Ic), with $R^2$=(If) is observed.

In a preferred embodiment, the compounds according to the invention comprise the compounds of formulae (Ia) and (Ib) and the ratio of compounds (Ia) and (Ib) is from 1:1.9 to 1.9:1, preferably 1:0.8 to 0.8:1 by weight.

To avoid byproducts, in particular oxidation products, the preparation of the substances of the formula (I) is preferably carried out under a stream of inert gas, preferably a stream of nitrogen. The products of the formulae (Ia)-(Ic) are generally obtained in good yield and with high degree of purity.

The substances of the formulae (Ia)-(Ic) and mixtures thereof are suitable as corrosion inhibitors, in particular in petroleum extraction and processing plants which come into contact with salt water. The amounts of these compounds used as corrosion inhibitors are from 1 to 200, preferably from 5 to 50, mg per liter of corrosive liquid. Since the compounds of the invention are usually prepared as highly viscous liquids, they are in practice normally used as a 20-50% by weight strength solution, for example in water, glycols, glycol ethers, alcohols and other suitable solvents. These solutions can also include other corrosion-inhibiting active ingredients and also emulsifiers, antifoaming agents and further customary additives which improve the useful properties of the product being applied.

In general, however, the corrosion-inhibiting effect of such mixtures is provided by the corrosion-inhibitor components of the invention alone.

PREPARATIVE EXAMPLES

Example 1

265.4 (0.5 mol) of N-coco alkyl-N'-poly(oxyalkyl)-(2-propyl-hexahydropyrimidine (A=—$C_2H_4$—, p=5) are initially charged in a stirred autoclave and heated to 55° C. under a stream of nitrogen. While stirring, methyl chloride (50.5 g, 1.0 mol) is added. The reaction temperature did not exceed 85° C. After the complete addition, the reaction mixture is stirred for 5 h at 80° C. After cooling to room temperature, 314.1 g of a brown, viscous liquid are obtained. Amine-value: 0.11%.

Example 2

294.5 g (0.5 mol) of N-coco alkyl-N'-poly(oxyalkyl)-(2-methyl-hexahydropyrimidine (A=(—$C_2H_4$—)$_3$(—$C_3H_6$—)$_3$, p=6) are initially charged in a stirred autoclave and heated to 55° C. under a stream of nitrogen. While stirring, methyl chloride (50.5 g; 1.0 mol) is added dropwise. The reaction temperature did not exceed 85° C. After the complete addition, the reaction mixture is stirred for 5 h at 80° C. After cooling to room temperature, 344.5 g of a brown, viscous liquid are obtained. Amine-value: 0.08%.

Example 3

156.0 g (0.5 mol) of N-coco alkyl-N'-poly(oxyalkyl)-hexahydropyrimidine (A=—$C_2H_4$—, p=1) are initially charged in a stirred autoclave and heated to 55° C. under a stream of nitrogen. While stirring, methyl chloride (50.5 g, 1.0 mol) is added. The reaction temperature did not exceed 85° C. After the complete addition, the reaction mixture is stirred for 5 h at 80° C. After cooling to room temperature, 206.1 g of a brown, viscous liquid are obtained. Amine-value: 0.08%.

Example 4

381.6 g (0.5 mol) of N-tallow alkyl-N'-poly(oxyalkyl)-hexahydropyrimidine (A=—$C_2H_4$—, p=10) are initially charged and heated to 55° C. under a stream of nitrogen. While stirring, 63.0 g (0.5 mol) dimethyl sulfate are added dropwise. The reaction temperature did not exceed 85° C. After the complete addition, the reaction mixture is stirred for 5 h at 80° C. After cooling to room temperature, 444.0 g of a brown, viscous liquid are obtained. Amine-value: 1.55%.

Example 5

269.1 g (0.330 mol) of N-tallow alkyl-N'-poly(oxyalkyl)-hexahydropyrimidine (A=—$C_2H_4$—, p=10) are initially charged and heated to 50° C. under a stream of nitrogen.

While stirring, 81.6 g (0.647 mol) dimethyl sulfate are added dropwise. The reaction temperature did not exceed 85° C. After the complete addition, the reaction mixture is stirred for 7.5 h at 80° C. After cooling to room temperature, 325.0 g of a brown, viscous liquid are obtained. Amine-value: 0.12%.

Example 6

200.3 g (0.5 mol) of N-coco alkyl-N'-poly(oxyalkyl)-(hexahydropyrimidine-2-carboxylic acid) (A=—$C_2H_4$—, p=2) are initially charged in a stirred autoclave and heated to 55° C. under a stream of nitrogen. While stirring, methyl chloride (50.5 g, 1.0 mol) is added. The reaction temperature did not exceed 85° C. After the complete addition, the reaction mixture is stirred for 5 h at 80° C. After cooling to room temperature, 250.6 g of a brown, viscous liquid are obtained. Amine-value: 0.10%.

Example 7

408.6 g (0.5 mol) of N-tall oil alkyl-N'-poly(oxyalkyl)-(2-propyl-hexahydropyrimidine) (A=—$C_2H_4$—, p=10) are initially charged in a stirred autoclave and heated to 55° C. under a stream of nitrogen. While stirring, allyl bromide (120.99 g, 1.0 mol) is added. The reaction temperature did not exceed 70° C. After the complete addition, the reaction mixture is stirred for 5 h at 70° C. After cooling to room temperature, 469.8 g of a brown, viscous liquid are obtained. Amine-value: 0.08%.

Example 8

691.9 g (0.5 mol) of N-lauryl-N'-poly(oxyalkyl)-(2-butyl-hexahydropyrimidine) (A=—$C_2H_4$—, p=25) are initially charged and heated to 55° C. under a stream of nitrogen. While stirring, benzyl chloride (31.65 g, 0.25 mol) is added. The reaction temperature did not exceed 85° C. After the complete addition, the reaction mixture is stirred for 5 h at 80° C. After cooling to room temperature, 723.2 g of a brown, viscous liquid are obtained. Amine-value: 1.43%.

Example 9

614.0 g (0.5 mol) of a N-alkyl-N'-poly(oxyalkyl)-(hexahydropyrimidine) of the formula X with A=—$C_2H_4$—, p=5, R1=behenyl, R2=I (g) with B=single bond, A=—$C_2H_4$—, p=5, R1=behenyl are initially charged in a stirred autoclave and heated to 55° C. under a stream of nitrogen. While stirring, methyl chloride (101.0 g, 2.0 mol) is added. The reaction temperature did not exceed 85° C. After the complete addition, the reaction mixture is stirred for 5 h at 80° C. After cooling to room temperature, 714.1 g of a brown, viscous liquid are obtained. Amine-value: 0.11%.

Example 10

508.8 g (0.5 mol) of a N-alkyl-N'-poly(oxyalkyl)-(hexahydropyrimidine) of the formula X with A=—$C_2H_4$—, p=5, R1=C-chain derived from coco fatty acid, R2=I (g) with B=C3-alkylene group, A=—$C_2H_4$—, p=5, R1=C-chain derived from coco fatty acid are initially charged in a stirred autoclave and heated to 55° C. under a stream of nitrogen. While stirring, methyl chloride (101.1 g, 2.0 mol) is added. The reaction temperature did not exceed 85° C. After the complete addition, the reaction mixture is stirred for 5 h at 80° C. After cooling to room temperature, 609.7 g of a brown, viscous liquid are obtained. Amine-value: 0.09%.

Corrosion Tests

Sour LPR Bubble Testing

The LPR bubble tests were conducted in 1 L Pyrex glass vessels that were continuously purged with 200 ppm $H_2S$ gas (contained in an oxygen free $CO_2/N_2$ gas matrix) and heated to 66° C. The testing solution comprised 900 mL of synthetic brine (Brine composition listed in Table 1) and deaerated overnight with $CO_2$ gas prior to saturation with 200 ppm $H_2S$ gas just before testing. Working electrodes made from 1018 carbon steel (CS) with a surface area of 4.785 $cm^2$ were polished with 600 grit silicon carbide paper and rinsed in acetone prior to insertion into the testing solution. A magnetic stir bar and hot plate combination was used to agitate and monitor heating of the solution for the duration of the tests. Flow meters were used to ensure the $H_2S$ flow rates were identical between all cells.

Linear polarization resistance (LPR) measurements were made with a Gamry electrochemical measurement system. A CS 1018 electrode was used as a pseudo-reference and a graphite rod was used as the counter electrode. The chemicals were added at 10 ppm based on the total solution volume (900 mL) after the baseline corrosion rates were monitored for continuity.

Typical Test Conditions:

| | |
|---|---|
| Gas Composition | 200 ppm $H_2S$, 20.4% $CO_2$, $N_2$ balance |
| Pressure | Ambient |
| Brine Composition | 900 mL 3.5% Seasalt Brine |
| Dose Rate | 10 ppm |
| Coupons | Carbon Steel |
| Test Duration | 24 hours |
| Stir Rate | 150 rpm |
| Temperature | 90° C. (194° F.) |

TABLE 1

Brine composition
The major constituents of sea water*
Chlorinity = 19.00 0/00†

| Ion | Parts per million | Equivalents per million | Parts per million per unit chlorinity |
|---|---|---|---|
| Chloride, $Cl^-$ | 18,980.0 | 535.3 | 998.90 |
| Sulfate, $SO_4^{--}$ | 2,649.0 | 55.1 | 139.40 |
| Bicarbonate, $HCO_3^-$ | 139.7 | 2.3 | 7.35 |
| Bromine, $Br^-$ | 64.6 | 0.8 | 3.40 |
| Fluoride, $F^-$ | 1.3 | 0.1 | 0.07 |
| Boric acid, $H_3BO_3$ | 26.0 | …‡ | 1.37 |
| Total | | 593.6 | |
| Sodium, $Na^+$ | 10,556.1 | 159.0 | 555.60 |
| Magnesium, $Mg^{++}$ | 1,272.0 | 104.6 | 66.95 |
| Calcium, $Ca^{++}$ | 400.1 | 20.0 | 21.06 |
| Potassium, $K^+$ | 380.0 | 9.7 | 20.00 |
| Strontium, $Sr^{++}$ | 13.3 | 0.3 | 0.70 |
| Total | | 593.6 | |

*H. U. Sverdrup, M. W. Johnson, and R. H Fleming, *The Oceans*, Prentice-Hall, Inc., New York, 1942. J. Lyman and R. H. Fleming, *J. Marine Research*, 3, 134-146, 1940.
†0/00 is used to denote grams per kilogram or parts per thousand.
‡ Undissociated at usual pH.

LPR screenings of multiple N-alkyl-N'-poly(oxyalkyl) hexahydropyrimidine-quaternary ammonium salt were conducted. These results are listed in Table 2.

TABLE 2

LPR Test Results for some N-alkyl-N'-poly(oxyalkyl)hexahydropyrimidine-quaternary ammonium salt derivatives

| Example | Corrosion Inhibitor | Corrosion rate after 2 hours [mpy] | Corrosion rate at final 2 hours [mpy] | % protection after 2 hours | % protection final 2 hours |
|---|---|---|---|---|---|
| 11 | CW1112[1] (comparative example) | 1.4 | 0.8 | 88.93 | 93.15 |
| 12 | N-tallowalkyl-N'-poly(oxyalkyl)-hexahydro-pyrimidine (A = —$C_2H_4$—, p = 10) (comparative example) | 1.7 | 0.8 | 74.88 | 87.99 |
| 13 | Example 1 | 1.2 | 0.8 | 90.32 | 96.54 |
| 14 | Example 2 | 1.4 | 1.1 | 88.43 | 92.34 |
| 15 | Example 3 | 1.4 | 0.8 | 90.74 | 94.20 |
| 16 | Example 4 | 1.1 | 0.1 | 91.85 | 98.88 |
| 17 | Example 5 | 0.9 | 0.1 | 93.50 | 99.34 |
| 18 | Example 6 | 1.5 | 0.7 | 89.36 | 94.42 |
| 19 | Example 7 | 1.2 | 0.3 | 91.74 | 98.73 |
| 20 | Example 8 | 1.3 | 0.6 | 90.45 | 95.34 |
| 21 | Example 9 | 1.4 | 0.6 | 90.36 | 94.42 |
| 22 | Example 10 | 1.1 | 0.2 | 91.61 | 98.90 |

[1]commercially available alkyl pyridine quaternary ammonium chloride (product name: CW 1112; manufacturers name: Oilfield Solutions Inc.; CAS: 68909-18-2).

Two known chemicals were used as comparative examples: CW 1112 is an alkyl pyridine quaternary ammonium chloride and a known corrosion inhibitor for sour corrosion. A comparative product (N-tallowalkyl-N'-poly(oxyalkyl)-hexahydropyrimidine (A=—$C_2H_4$—; p=10) was used as another comparison. The N-alkyl-N'-poly(oxyalkyl) hexahydropyrimidine-quaternary ammonium salt derivatives were tested against the benchmark products. The chemicals performed in a superior manner to the comparative chemicals.

High Pressure and High Temperature Sour Autoclave Tests

Autoclaves equipped with rotating cage (RCA) were used to simulate the high shear conditions for the purpose of evaluating system corrosivity as well as inhibitor performance. The test solution, consisting of 800 mL of synthetic brine was deaerated with $CO_2$ overnight before pressurizing into the autoclaves using $CO_2$. Three weight loss corrosion coupons fixed on the rotating cage were used in each autoclave. The pit formation and pit density were analyzed by a high-powered microscope. General corrosion rates were calculated by weight loss measurement. Test conditions are summarized below.

Typical Test Conditions:

| | |
|---|---|
| Gas Composition | 200 ppm $H_2S$, 20.4% $CO_2$, $N_2$ balance |
| Pressure | 330 psi (23 bar) |
| Brine Composition | 800 mL 3.5% Seasalt Brine |
| Dose Rate | 15 ppm |
| Coupons | 1018 Carbon Steel |
| Test Duration | 3 days |
| Stir Rate | 1000 rpm |
| Temperature | 90° C. (194° F.) |

The results of the more rigorous testing in sour conditions available with rotating cage autoclaves for two corrosion inhibitor candidates is shown in Table 3.

TABLE 3

Weight Loss Analyses For Sour Rotating Cage Autoclave Testing and Localized Corrosion in the Presence of Example 5 and Comparative Samples

| Product | Example | Coupon Number | Weight (g) Initial | Weight (g) Post | Weight Loss (g) | Average Corrosion Rate (mpy) | Average Pit Frequency (>10 μm) |
|---|---|---|---|---|---|---|---|
| N-tallow alkyl-N'-poly(oxy-alkyl)-hexa-hydropyrimidine (A = —$C_2H_4$—, p = 10) (comparative example) | 23 | 8 | 15.7804 | 15.7501 | 0.0303 | 5.74 | 80/cm² |
| | 24 | 9 | 15.2362 | 15.2085 | 0.0277 | 5.23 | |
| | 25 | 10 | 15.2692 | 15.2440 | 0.0252 | 4.77 | |
| CW 1112[1] (comparative example) | 26 | 11 | 15.6108 | 15.5716 | 0.0392 | 7.41 | 164/cm² |
| | 27 | 12 | 15.6743 | 15.6367 | 0.0376 | 7.10 | |
| | 28 | 13 | 14.9125 | 14.8769 | 0.0356 | 6.74 | |
| Example 5 | 29 | 41 | 16.1274 | 16.1162 | 0.0112 | 2.12 | 57/cm² |
| | 30 | 42 | 16.5483 | 16.5375 | 0.0108 | 2.05 | |
| | 31 | 57 | 15.6877 | 15.6763 | 0.0115 | 2.17 | |

TABLE 3-continued

Weight Loss Analyses For Sour Rotating Cage Autoclave Testing and Localized Corrosion in the Presence of Example 5 and Comparative Samples

| Product | Example | Coupon Number | Weight (g) Initial | Weight (g) Post | Weight Loss (g) | Average Corrosion Rate (mpy) | Average Pit Frequency (>10 µm) |
|---|---|---|---|---|---|---|---|
| Blank | Uninhibited | 195 | 16.6176 | 15.9912 | 0.62643 | 71.07 | Numerous |
|  | Uninhibited | 196 | 16.2791 | 15.5866 | 0.69250 | 78.56 |  |
|  | Uninhibited | 197 | 16.4948 | 15.8014 | 0.69337 | 78.66 |  |

[1]commercially available alkyl pyridine quaternary ammonium chloride (product name: CW 1112; manufacturers name: Oilfield Solutions Inc.; CAS: 68909-18-2).

Benchmark chemicals CW1112 (commercially available alkyl pyridine quat) and a comparative compound (N-tallow-alkyl-N'-poly(oxyalkyl)-hexahydropyrimidine; A=—$C_2H_4$—, p=10) were tested against "Example 5" (Table 3) as defined above. RCA tests were repeated several times under varying conditions with similar results to those shown in Table 3.

A further understanding of the presently claimed invention can be gained from the detailed description, taken in conjunction with the accompanying drawings of which:

The order of lowest pit depth and pit density to highest pit depth density was "Example 5"<"N-tallow alkyl-N'-poly(oxyalkyl)-hexahydropyrimidine (A=—$C_2H_4$—, p=10)"<"CW1112".

A benchmark formulation A (see Table 5) containing a non-quaternized N-tallow alkyl-N'-poly(oxyalkyl)-hexahydropyrimidine (A=—$C_2H_4$—, p=10) was tested against a formulation B (see Table 6) which contains 14 wt % Example 5.

The LPR Test Results are shown in Table 4. The results show that formulation B provides better corrosion protection than formulation A.

TABLE 4

LPR Test Results for formulated products.

| Example | Formulation | Corrosion rate after 2 hours [mpy] | Corrosion rate at final 2 hours [mpy] | % protection after 2 hours | % protection final 2 hours |
|---|---|---|---|---|---|
| 1 | A (comparative example) | 1.5 | 1.3 | 0.6 | 16.5 |
| 2 | B | 1.3 | 1.0 | 56.7 | 65.9 |

TABLE 5

Formulation A

| Raw material | CAS No. | Content [wt %] |
|---|---|---|
| Butylglycol | 111-76-2 | 20 |
| N-tallowalkyl-N'-poly(oxyalkyl)-hexahydropyrimidine | Trade secret | 14 |
| Glacial acetic acid | 64-19-7 | 2 |
| Water | 7732-18-5 | 50 |
| Quaternary salt | Trade secret | 7 |
| Complex amine | Trade secret | 7 |

TABLE 6

Formulation B

| Raw material | CAS No. | Content [wt %] |
|---|---|---|
| Butylglycol | 111-76-2 | 20 |
| Example 5 | Defined above | 14 |
| Glacial acetic acid | 64-19-7 | 2 |
| Water | 7732-18-5 | 50 |
| Quaternary salt | Trade secret | 7 |
| Complex amine | Trade secret | 7 |

The invention claimed is:

1. N-alkyl-N'-poly(oxyalkyl)hexahydropyrimidine-quaternary ammonium salts of the formulae (Ia)-(Ic)

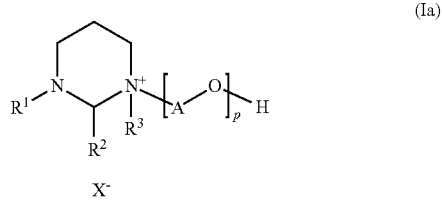

(Ia)

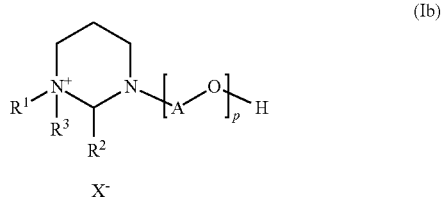

(Ib)

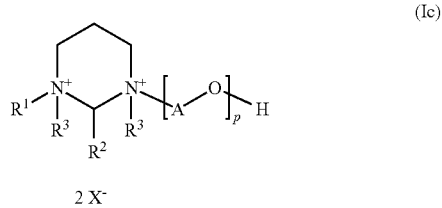

(Ic)

in which $R^1$ is $C_8$-$C_{30}$-alkyl or $C_8$-$C_{30}$-alkenyl, $R^2$ is hydrogen, $C_1$-$C_3$-alkyl, —COOH or a group selected from the formulae

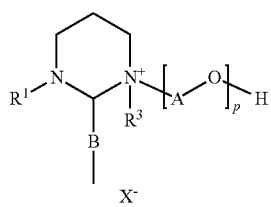
(Id)

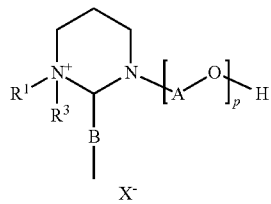
(Ie)

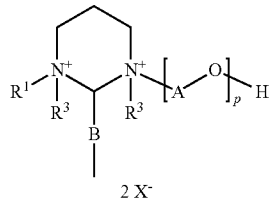
(If)

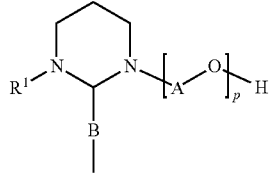
(Ig)

wherein
the bonding occurs via the valence containing the B residue,
B is a single bond or a $C_1$ to $C_3$ alkylene group
$R^3$ is $C_1$-$C_4$-alkyl, vinyl, allyl or benzyl,
$X^-$ is a counterion,
A is a 1,2-alkylene group having from 2 to 10 carbon atoms and
p is a number from 1 to 50.

2. A compound according to claim 1, wherein $R^1$ is $C_9$-$C_{24}$-alkyl, or $C_9$-$C_{24}$-alkenyl.

3. A compound according to claim 1, wherein $R^3$ is methyl.

4. A compound according to claim 1, wherein $R^2$ is hydrogen.

5. A compound as claimed in claim 1, wherein A is ethylene.

6. A compound as claimed in claim 1, wherein the degree of alkoxylation p is between 5 to 15 on average.

7. A compound according to claim 1, comprising compounds of formula (Ia) and (Ib) and wherein the ratio of compounds (Ia) and (Ib) is from 1:1.9 to 1.9:1 by weight.

8. A corrosion inhibitor formulation comprising at least one compound according to claim 1.

9. A process for inhibiting corrosion of metal, the process comprising bringing the metal into contact with at least one compound comprising N-alkyl-N'-poly(oxyalkyl)hexahydropyrimidine-quaternary ammonium salts of the formulae (Ia)-(Ic)

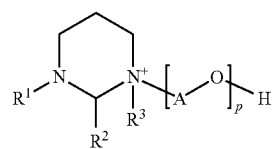
(Ia)

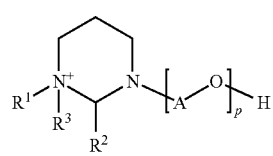
(Ib)

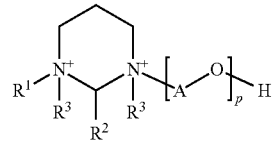
(Ic)

in which
$R^1$ is $C_8$-$C_{30}$-alkyl or $C_8$-$C_{30}$-alkenyl,
$R^2$ is hydrogen, $C_1$-$C_3$-alkyl, —COOH or a radical selected from the formulae

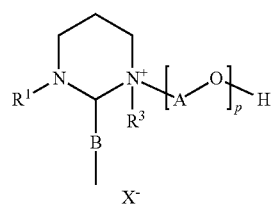
(Id)

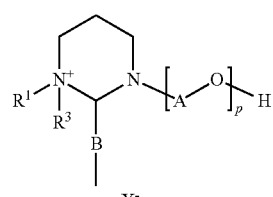
(Ie)

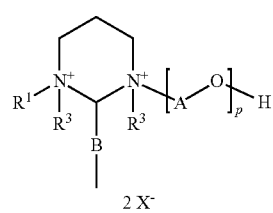
(If)

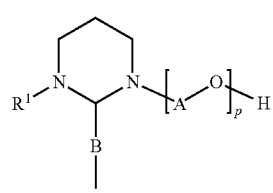
(Ig)

wherein
the bonding occurs via the valence containing the B residue,

B is a single bond or a $C_1$ to $C_3$ alkylene group $R^3$ is $C_1$-$C_4$-alkyl, vinyl, allyl or benzyl, $X^-$ is a counterion, A is a 1,2-alkylene group having from 2 to 10 carbon atoms and p is a number from 1 to 50.

10. The process of claim 9, wherein the metal is in contact with sour gas during crude oil or natural gas production or processing.

\* \* \* \* \*